(12) United States Patent
Steffensmeier et al.

(10) Patent No.: US 7,172,599 B2
(45) Date of Patent: Feb. 6, 2007

(54) TIBIAL SIZER

(75) Inventors: Scott Steffensmeier, Warsaw, IN (US); Jeffrey Michael, Richland, MI (US)

(73) Assignee: Zimmer Technology, Inc., Chicago, IL (US)

( * ) Notice: Subject to any disclaimer, the term of this patent is extended or adjusted under 35 U.S.C. 154(b) by 220 days.

(21) Appl. No.: 10/792,337

(22) Filed: Mar. 3, 2004

(65) Prior Publication Data

US 2005/0203541 A1  Sep. 15, 2005

(51) Int. Cl.
*A61B 17/60* (2006.01)

(52) U.S. Cl. ............... 606/102; 33/512; 623/20.14

(58) Field of Classification Search ........... 606/102, 606/86, 53; 33/512, 700
See application file for complete search history.

(56) References Cited

U.S. PATENT DOCUMENTS

| | | | | | |
|---|---|---|---|---|---|
| 1,011,628 | A | * | 12/1911 | Klein | 33/2 H |
| 1,431,873 | A | * | 10/1922 | Clausing | 33/3 A |
| 1,962,518 | A | * | 6/1934 | Nessler | 33/512 |
| 1,981,911 | A | * | 11/1934 | Engelsman | 33/512 |
| 2,531,477 | A | * | 11/1950 | Smith | 33/3 A |
| 3,197,875 | A | * | 8/1965 | D Azzo | 33/512 |
| 3,300,864 | A | * | 1/1967 | Lesslie | 33/512 |
| 4,211,228 | A | * | 7/1980 | Cloutier | 606/102 |
| 4,759,350 | A | * | 7/1988 | Dunn et al. | 606/82 |
| 6,063,091 | A | * | 5/2000 | Lombardo et al. | 606/88 |
| 6,979,299 | B2 | * | 12/2005 | Peabody et al. | 600/587 |
| 2004/0122441 | A1 | * | 6/2004 | Muratsu | 606/102 |

OTHER PUBLICATIONS

Intramedullary Surgical Approach—The M/G™ Unicompartmental Knee Minimally Invasive Surgical Technique; by Zimmer, Inc., 2002; pp. 1-24 (with special emphasis directed to p. 18).

* cited by examiner

*Primary Examiner*—Eduardo C. Robert
*Assistant Examiner*—James L. Swiger
(74) *Attorney, Agent, or Firm*—Baker & Daniels LLP

(57) ABSTRACT

A tibial sizer, or set of sizers, used to estimate the appropriate size tibial base plate implanted during knee arthroplasty. The preferred embodiment provides a measurement of the amount of exposed bone between a posterior proximal portion of the tibia and a posterior edge of the tibial sizer (which edge will correspond to the posterior edge of the tibial base plate). Preferably, the sizer includes a head and a handle extending outwardly from the head, as well as a channel with a slider configured and arranged to be slidably positioned within the channel. The slider includes markings for indicating the amount of exposed bone between a posterior proximal portion of a tibia and a posterior edge of the head of the sizer. Additional markings are also provided for indicating a suggested size of tibial base plate with respect to the anterior/posterior direction.

10 Claims, 4 Drawing Sheets

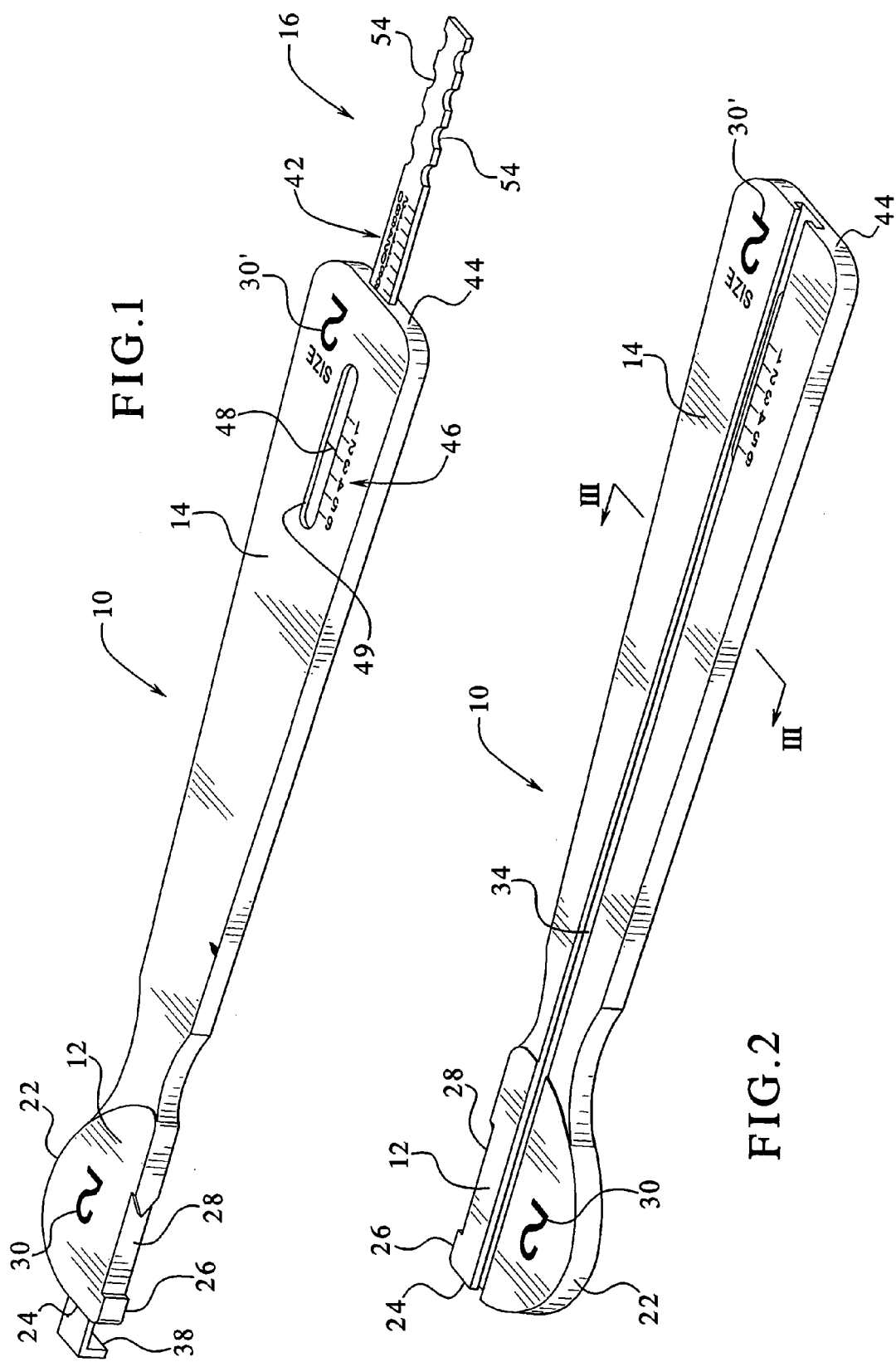

TIBIAL SIZER

The present invention relates generally to an instrument for helping to estimate the appropriate size tibial base plate implanted during knee arthroplasty surgery. More particularly, the present invention relates to one or more tibial sizers, and a method of using the sizers, where the sizers are used to estimate the appropriate size tibial base plate, with respect to both the anterior/posterior direction and the medial/lateral direction. Additionally, the preferred embodiment also provides a measurement of the amount of exposed bone between a posterior proximal portion of the tibia and a posterior edge of the tibial sizer (which edge will correspond to the posterior edge of the tibial base plate of the corresponding size).

BRIEF SUMMARY OF THE INVENTION

Briefly, the present invention relates to a tibial sizer for use during knee arthroplasty. The embodiment described herein is intended to be utilized during unicompartmental knee arthroplasty (UKA). However, the concept of the present invention could also be applied to other types of knee arthroplasty, such as total knee arthroplasty (TKA). The preferred embodiment of the tibial sizer includes a head and a handle extending outwardly from the head. There is preferably a channel that extends along the tibial sizer in a longitudinal direction, through at least a portion of the head and at least a portion of the handle, with a slider configured and arranged to be slidably positioned within the channel. In the preferred embodiment, the head includes posterior, lateral and medial outer peripheral surfaces. The posterior outer peripheral surface is generally flat, and one of the lateral outer peripheral surface or the medial outer peripheral surface is curved and the other of the lateral outer peripheral surface and the medial outer peripheral surface is generally flat and includes a cutout portion therein.

Several sets of markings are preferably provided on the tibial sizer. There is preferably a first set of markings for indicating the amount of exposed bone between a posterior proximal portion of a tibia and a posterior edge of the head of the tibial sizer. Additionally, there is also preferably a second set of markings for indicating a suggested size of tibial base plate with respect to an anterior/posterior direction, which markings are used when the slider is inserted into the channel of the tibial sizer. Optionally, the slider may be configured to be used, for some measurements, without being inserted into the channel. For this feature, the slider includes a third set of markings that comprise indicia representing different sizes of tibial base plates, wherein the third set of markings are for determining a suggested size of tibial base plate, with respect to the anterior/posterior direction, when the slider is used without being inserted into the tibial sizer.

The present invention also relates to a method of using the tibial sizer, as well as to a system of tibial sizers of a plurality of different sizes. Preferably, the system of sizers only includes a single slider, which can be used with each of the sizers, or the slider can also be used alone (for certain measurements).

BRIEF DESCRIPTION OF THE DRAWINGS

Preferred embodiments of the present invention are described herein with reference to the drawings wherein:

FIG. 1 is a perspective view of one side of one preferred embodiment of the tibial sizer of the present invention, shown with the slider inserted into the channel;

FIG. 2 is a perspective view of the tibial sizer of FIG. 1, shown from the opposite side and without the slider;

DETAILED DESCRIPTION OF THE INVENTION

Figure 5:
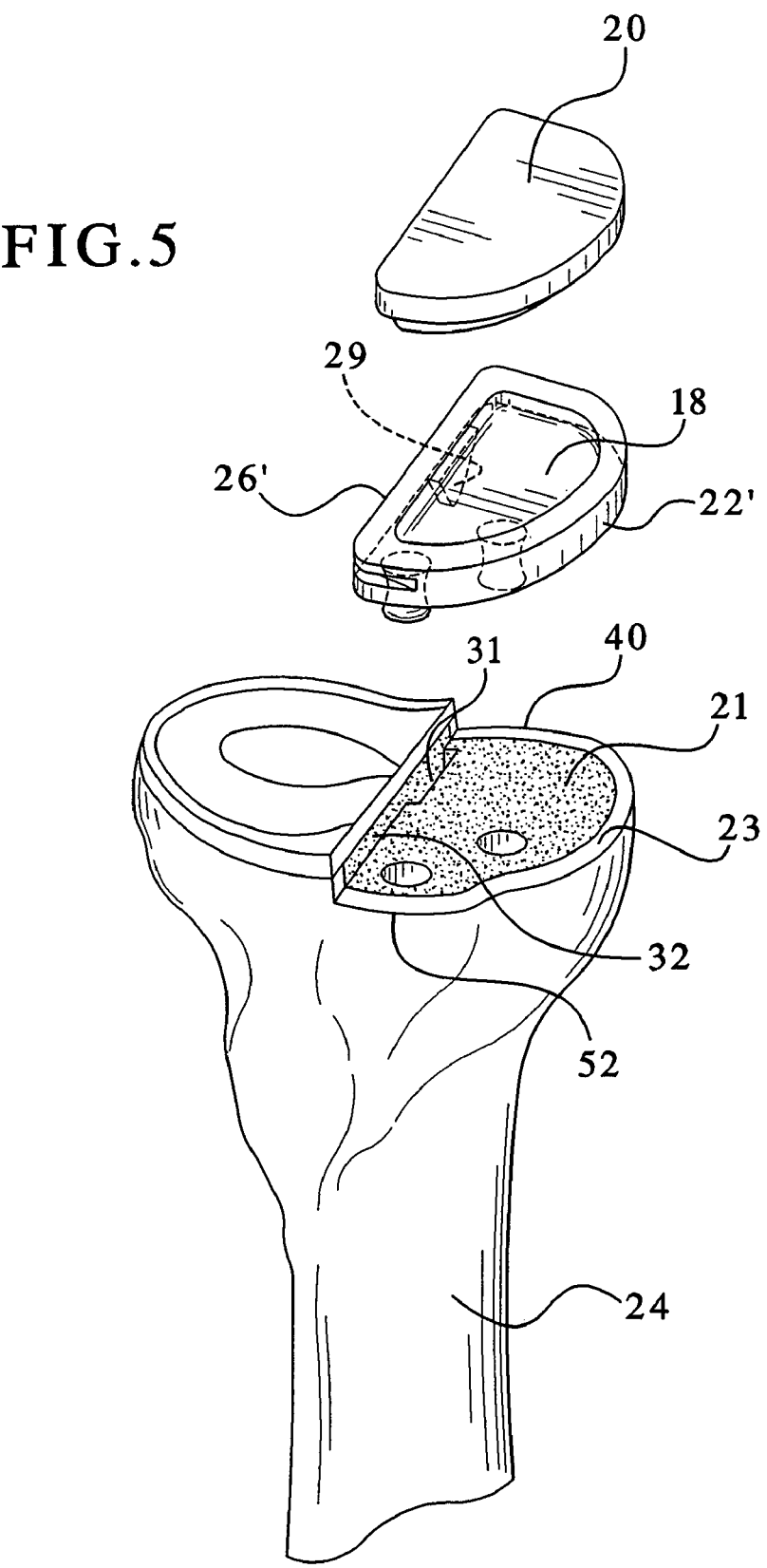
FIG. 5 is a view of a resected tibia, shown with an example of a tibial base plate of a unicompartmental knee prosthesis.

Turning now to FIGS. 1 and 2, a preferred embodiment of the present tibial sizer 10 is shown. The sizer includes a head 12 and a handle 14, as well as a separate slider 16 that is configured to slide within the head and handle. Turning first to the head 12, the outer periphery of the head is shaped to correspond to the outer periphery of a tibial base plate, one example of which is shown in FIG. 5 and is designated as base plate 18. In the depicted example, tibial base plate 18 is configured for use with a plastic insert 20. However, the present invention may also be used with other types of tibial base plates, such as those of unitary construction whereby the insert is not a separate component. As shown in FIG. 5, the tibial base plate 18 is intended to be implanted into the resected portion 21 of a tibia 24.

The tibial sizer 10 is capable of being used on both the left and the right tibia, and on either the medial compartment or the lateral compartment of either tibia. However, for the sake of convenience in description, the tibial sizer will primarily be shown and described with respect to the medial compartment of the right tibia, and the terms lateral, medial, etc. relative to the right tibia will be used. Of course, if the prosthesis was being implanted into the left tibia, the surfaces on the prosthesis and the tibial sizer designated as lateral and medial would be reversed.

Figure 6:
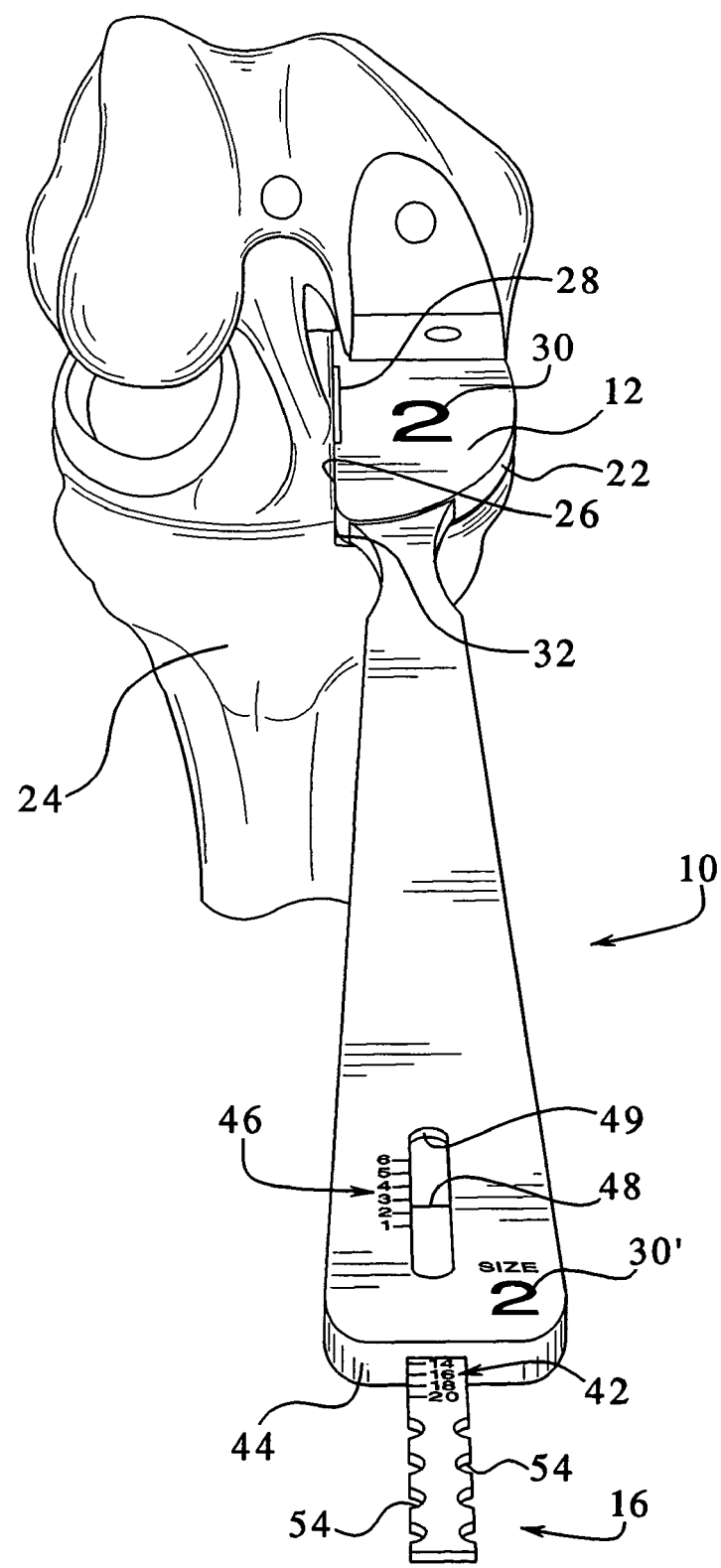
FIG. 6 is a view of the tibial sizer of FIG. 1 positioned upon the cut surface of a resected tibia.

FIG. 1 shows the tibial sizer 10 as it would be positioned for use in the medial compartment of the right tibia, and FIG. 6 shows the tibial sizer in such a position. Head 12 includes a curved outer peripheral surface 22 connected to a generally flat posterior outer peripheral surface 24, which is itself connected to another generally flat outer peripheral surface 26. In this orientation (for use with the medial compartment of the right tibia), the curved outer peripheral surface 22 is the medial outer peripheral surface of head 12, and surface 26 is the lateral outer peripheral surface of the head. Optionally, the generally flat lateral outer peripheral surface 26 includes a cutout portion 28, which can be used as a guide to create a cut, or to mark the position of a cut, to accommodate a keel on a tibial implant (such as keel 29 shown in FIG. 5), as described more fully below.

The outer peripheral surfaces 22, 24, and 26 of the tibial sizer are shaped and sized like the corresponding outer peripheral surfaces of the tibial base plate 18 of FIG. 5. More specifically, curved outer peripheral surface 22 of the sizer 10 (FIG. 1) corresponds to curved outer peripheral surface 22' of base plate 18 (FIG. 5) and generally flat outer peripheral surface 26 of the sizer 10 (FIG. 1) corresponds to generally flat outer peripheral surface 26' of base plate 18 (FIG. 5). Additionally, generally flat posterior outer peripheral surface 24 of the sizer 10 corresponds to the generally flat posterior outer peripheral surface of the base plate 18 (which surface is hidden from view in FIG. 5).

In order to accommodate the range of sizes of tibial base plates, there should be a set of tibial sizers with heads 12 of a variety of different sizes, with one head corresponding in size to each size of tibial base plate 18. For example, if there are six different sizes of tibial base plate 18, there should be six different sizes of tibial sizer 10. In order to readily show the size of a particular tibial sizer, size markings such as markings 30 and 30' should be provided on at least one location, and preferably at two locations, as shown in FIG. 1. Further, the size markings 30/30' should coincide with the size markings on the tibial base plates. For example, where there are six different sizes of tibial base plate to select from, designated as "Size 1", "Size 2", "Size 3", "Size 4", "Size 5" and "Size 6", the six corresponding tibial sizers 10 should also be designated as "Size 1", "Size 2", etc.

Although different sizes of tibial sizers should be provided, each sizer can be used for any one of the four compartments (i.e., lateral compartment of the right tibia, medial compartment of the right tibia, lateral compartment of the left tibia, and medial compartment of the left tibia). More specifically, the orientation shown in FIG. 1 is used for the medial compartment of the right tibia and for the lateral compartment of the left tibia; and the orientation shown in FIG. 2 (which is merely the slider of FIG. 1 turned upside down) is used for lateral compartment of the right tibia and for the medial compartment of the left tibia.

In use, to determine the proper size tibial base plate to be implanted, different sized sizers 10 are placed on the resected portion 21 (FIG. 5) of the tibia 24, as shown in FIG. 6. The tibial sizer 10 should be placed with the flat outer peripheral surface 26 (which in this case is the lateral surface, since FIG. 5 shows the right tibia 24) against the surface 32 created by the sagittal cut. The tibial sizer 10 of the size that best covers the resected proximal tibia, without any overhang, should be selected. Care should be taken to ensure that the selected tibial sizer rests on cortical bone around its entire perimeter, without any overhang of the head 12, in order to ensure that the tibial base plate has strong cortical support.

The present tibial sizer 10 also includes a feature for measuring the amount of exposed bone posterior to the sizer, as well as including markings for providing a suggested size of tibial base plate with regard to the anterior/posterior direction. This anterior/posterior size suggestion provided by the markings described below should be used in conjunction with the anterior/posterior size estimate provided by matching the size of the head 12 (in the anterior/posterior direction) with the size of the resected portion 21 of the tibia, as described above. In the preferred embodiment of the present invention, the size estimate in the medial/lateral direction is provided by matching the size of the head 12 (in the medial/lateral direction) with the size of the resected portion 21 of the tibia, as described above.

Figure 3:
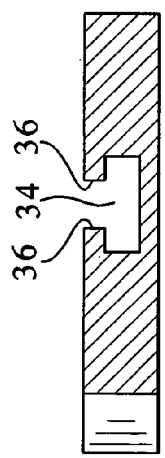
FIG. 3 is a cross-sectional view of the tibial sizer of FIG. 1, taken along line III—III of FIG. 2, showing the channel for receiving the slider.
Figure 4:
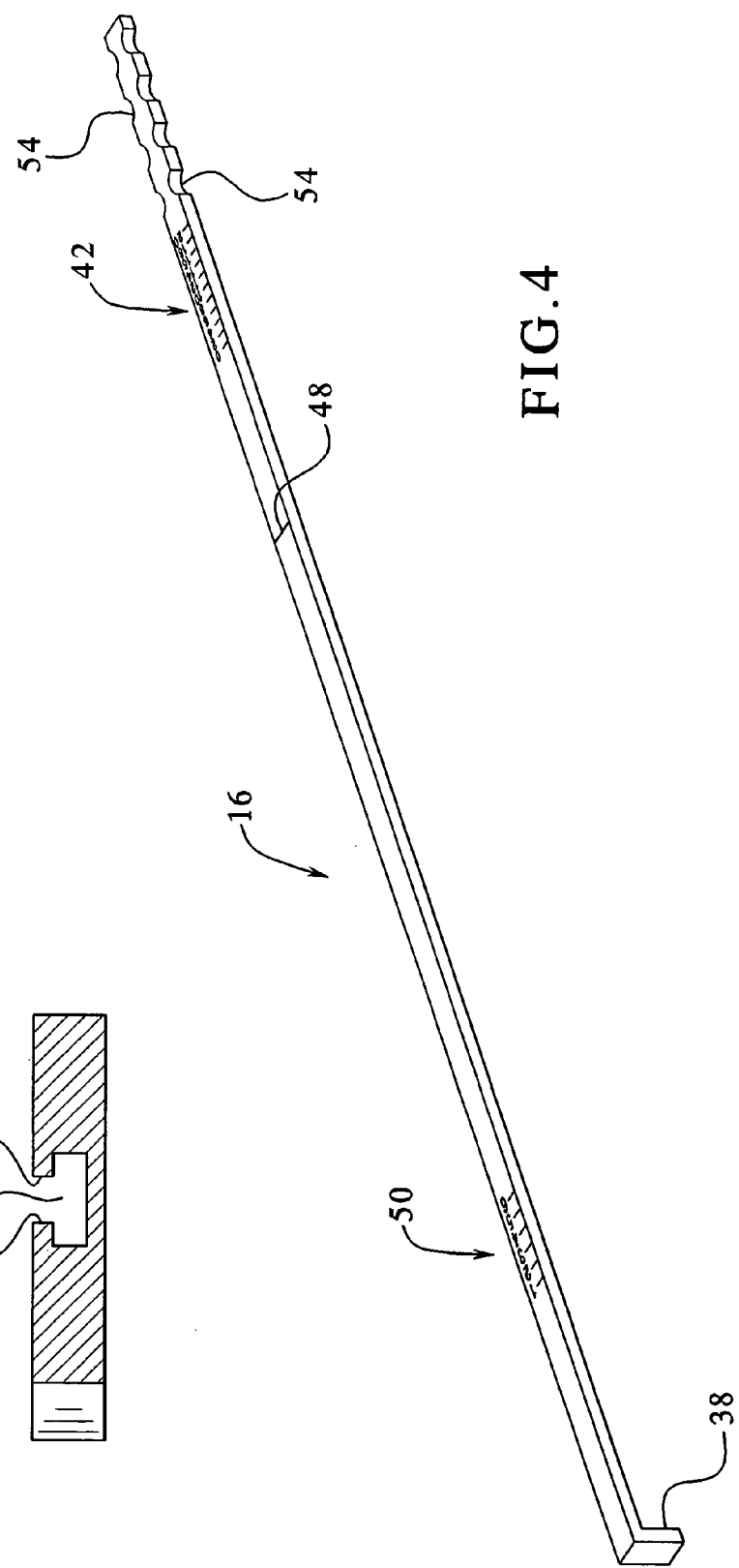
FIG. 4 is a perspective view of the slider, without the remainder of the tibial sizer.

The amount of exposed bone posterior to the sizer is indicated by the slider 16, which is shown inserted into the sizer 10 in FIG. 1, and is shown removed from the sizer in FIG. 4. The slider 16 is configured to slide within a channel 34 (FIG. 2) that extends along the longitudinal direction of 11 both the head 12 and the handle 14. FIG. 3 shows a cross-sectional view of the handle 14 taken along lines III—III of FIG. 2. This cross-sectional view clearly shows the channel 34, which also includes upper lips 36 for maintaining the slider 16 within the channel 34. The channel 34 is preferably configured to allow for the slider 16 to be easily removed, such as by simply pulling the slider out of the channel via a hook portion 38.

As mentioned above, the present invention relates to a set of different sized tibial sizers 10, with one sizer sized to correspond to each available size of tibial base plate 18. Optionally, one slider 16 may be provided for each tibial sizer 10. In the alternative, only one slider 16 could be provided for all of the different sized tibial sizers. Thus, for example, if a set of tibial sizers includes heads 12 of six different sizes, the single slider 16 provided with the set could be configured to fit all of the sizers, and it could simply be moved into the channel of the sizer being used. Preferably, the slider (or sliders) and the sizers are all made of stainless steel, although other materials are also contemplated as being within the scope of the invention.

The hook portion 38 of the slider 16 is configured to make contact with a posterior proximal portion 40 of the tibia 24 (see FIG. 5). When the slider 16 is inserted into the channel 34, and with the hook portion 38 making contact with the posterior proximal portion 40 and the head 12 properly aligned on the resected portion 21, two different sets of markings may be used—one set for indicating the amount of exposed bone posterior to the sizer; and another set for providing a suggested size of tibial base plate, with respect to the anterior/posterior direction. As shown in FIGS. 1 and 6, the first set of markings, designated as markings 42, indicate the amount of exposed bone between the posterior proximal portion 40 of the tibia 24 and the posterior outer peripheral surface 24 of the tibial sizer 10. More specifically, markings 42 are located on the slider 16, and provide the indication of exposed bone when viewed with respect to edge 44 of the handle 14 of the sizer 10. In the embodiment shown, markings 42 are provided in millimeters, between 0 mm and 20 mm, in 2 mm increments. Of course, any desired units may be used, and other increments between units are also contemplated. Markings 42, as well as the other types of markings described herein may be produced upon the sizer by a variety of different methods, such as laser etching, engraving, printing, etc.

The second set of markings, designated as markings 46 in FIGS. 1 and 6, provide a suggested size of tibial base plate, with respect to the anterior/posterior direction. Markings 46 include indicia on the handle 14 representing different sizes of tibial base plates and a pointer 48 on the slider 16 for pointing to indicate a suggested size of tibial base plate, with respect to the anterior/posterior direction and with the amount of exposed bone indicated by the first set of markings 42. As can be seen in FIGS. 1 and 6, the pointer 48 is visible through a window 49 that is provided in the handle 14. However, when the tibial sizer 10 is used in the orientation shown in FIG. 2, a window is unnecessary because channel 34 is open on this side of the sizer. In the example shown in FIGS. 1 and 6, there are six different sizes of tibial base plates (numbered from 1 to 6). However, a different amount and/or a different type of indicia may be provided if the number of tibial base plates is different from six and/or if the different sizes of tibial base plates are represented by a different designation system, such as alphabetically.

In use, the second set of markings 46 operates as follows. The head 12 of the appropriately sized tibial sizer 10 is positioned on the resected portion 21 of the tibia, with the flat outer peripheral surface 26 against the surface 32 created by the sagittal cut (FIGS. 5 and 6). The head 12 should be aligned so that its outer peripheral surfaces 22 and 24 do not extend beyond the bone, but instead rest on cortical bone, as mentioned above. If the outer peripheral surfaces 22 or 24 do extend beyond the bone, a smaller sizer should be selected. On the other hand, if the head 12 is so small that outer peripheral surfaces 22 and/or 24 are too small to rest on cortical bone, a larger sizer should be selected. After aligning the head 12 of the properly sized sizer 10, the slider 16 is slid within the channel 34 until the hook portion 38 makes contact with the posterior proximal portion 40 (FIG. 5) of the tibia 24. In order to facilitate gripping the slider, the slider 16 may optionally include a series of indentations 54 on the lateral and medial edges. With the hook portion 38 contacting posterior proximal portion 40, the pointer 48 on the slider 16 will point to indicia 46 on the handle 14 to suggest a size of tibial base plate, with respect to the anterior/posterior direction and with the amount of exposed bone indicated by the first set of markings 42. If a different amount of exposed bone is desired, the sizer 10 should be moved in the appropriate direction (i.e., the anterior direction or the posterior direction), and a different size of tibial base plate may be suggested (depending upon how much the amount of exposed bone is changed). The information provided by the second set of markings 46 (which provides size information for the anterior/posterior direction only) should be used in conjunction with the visual indication of the suggested size of tibial base plate from the head 12 being positioned on the resected portion 21 of the tibia (which provides size information for both the anterior/posterior direction and the media/lateral direction) to select a tibial base plate of an appropriate size.

Optionally, the slider may also include a third set of markings representing different sizes of tibial base plates indicating a suggested size of tibial base plate (with respect to the anterior/posterior direction), where the third set of markings are only usable if the slider 16 is used by itself, such as shown in FIG. 4. The third set of markings, designated as markings 50 in FIG. 4, includes the same indicia as the second set of markings 46 (except without the pointer 48). Thus, for example, the third set of markings 50 may be the numbers 1 through 6, which correspond to different sizes of tibial base plates. Of course, indicia other than the numbers 1 through 6 may also be used for the third set of markings.

In use, the third set of markings 50, which are visible when the slider 16 is used alone, operate as follows. The slider 16 (FIG. 4) is positioned upon the resected portion 21 (FIG. 5) of the tibia, with its hook portion 38 contacting the posterior proximal portion 40 of the tibia 24. The size of tibial base plate indicated by the one of the markings 50 closest to the anterior proximal portion 52 (FIG. 5) of the tibia 24 is the suggested size of tibial base plate, with respect to the anterior/posterior direction. Using the slider alone does not provide information for a suggested size of tibial base plate with respect to the medial/lateral direction, nor does it provide information regarding the amount of exposed bone between a posterior proximal portion of the tibia and a posterior edge of the head the tibial sizer (and/or the tibial base plate).

To facilitate understanding of the present invention, a brief description of the use of a set of tibial sizers will be provided next. Although this description will refer to unicompartmental knee arthroplasty (UKA) of the medial compartment of the right tibia, the tibial sizers of the present invention are also configured to be used on the lateral compartment of the right tibia (by orienting the sizer 10 as shown in FIG. 2), as well as on the lateral compartment of the left tibia (FIG. 1 orientation) and the medial compartment of the left tibia (FIG. 2 orientation). As mentioned earlier, the concepts of the present invention may also be applied to other types of knee surgery, such as total knee arthroplasty (TKA).

After the tibia has been resected, as shown in FIG. 5, the surgeon views the resected portion 21 and roughly estimates the appropriate size of tibial base plate needed, and selects (from a set of tibial sizers of different sizes) a tibial sizer 10 of a size that corresponds to a tibial base plate of the estimated size. As shown in FIG. 6, the surgeon then places the head 12 of the selected tibial sizer 10 on the cut surface 21 of the resected tibia so that the generally flat outer peripheral surface 26 (i.e., the lateral surface) of the head 12 of the tibial sizer 10 is against a surface 32 created by a sagittal cut. Next, the surgeon verifies that the outer medial periphery 22 of the head 12 sufficiently covers the resected tibia, without extending beyond cortical bone 23 (FIG. 5). If the outer medial periphery 22 of the head 12 does not provide appropriate coverage, the surgeon selects another tibial sizer 10 of a different size, and performs the verifying step again with the newly selected tibial sizer. If necessary, additional sizers are selected until the appropriate size has been found.

When the appropriate size of tibial sizer has been found, the slider 16 is inserted into the channel 34. Of course, the slider may be inserted into the channel earlier, if desired. With the slider 16 within the channel 34, the slider is slid until the hook 38 found on a slider 16 contacts a posterior edge 40 of the tibia 24. The surgeon then views a first set of markings 42 that indicate the amount of exposed bone between the posterior proximal portion 40 of the tibia 24 and the posterior edge 24 of the head 12 of the tibial sizer 10. If the amount of bone exposed is too high or too low, the surgeon may choose to select a different size tibial base plate than the size that corresponds to the tibial sizer being used. If a size change is needed, the steps described may be repeated with a sizer that corresponds to the newly chosen size.

In addition to viewing the way the head 12 corresponds to the resected portion 21 of the tibia, additional information about a suggested size of tibial base plate, with respect to the anterior/posterior direction, is provided by the surgeon's viewing of a second set of markings 46. The surgeon considers the position of the pointer 48 along indicia 46, which indicates suggested different sizes of tibial base plates for the amount of exposed bone indicated by the first set of markings 42. Finally, in light of the sizing information obtained by the surgeon when: (1) viewing the correspondence between the head 12 and the resected portion 21; (2) considering the amount of exposed bone indicated by markings 42; and (3) considering the suggested size of tibial base plate, with respect to the anterior/posterior direction, indicated by markings 46, the surgeon determines the appropriate size of tibial base plate to use. Then, the tibial base plate of the selected size is implanted using any desired method, and the arthroplasty continues as known to those of ordinary skill in the art.

If desired, the surgeon may also opt to use the cutout portion 28 on the head 12 of the tibial sizer 10 as a guide for either marking a desired location of a cut to accept a keel (such as keel 29 of FIG. 5) of the tibial implant or for directly creating a cut to accept the keel 29. More specifically, the head 12 of the sizer is positioned on the resected portion 21 (FIG. 5) of the tibia, and it is properly aligned, as shown in FIG. 6. If marking is desired, the surgeon merely uses the cutout portion 28 as a guide to mark the bone, using known marking methods, and the bone is then cut or punched using known methods, where it was marked, in order to provide a space 31 for the keel 29 of the tibial implant. On the other hand, if the surgeon wants to directly cut the space 31 for the keel 29, he/she may use the cutout portion 28 directly for guiding the saw blade used to make the space for the keel.

While various embodiments of the present invention have been shown and described, it should be understood that other modifications, substitutions and alternatives may be apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A tibial sizer for use during knee arthroplasty, said tibial sizer comprising:
 a head;
 a handle extending outwardly from said head;
 a channel extending along said tibial sizer in a longitudinal direction, through at least a portion of said head and at least a portion of said handle; and
 a slider configured and arranged to be slidably positioned within said channel, such that said slider is slidable within both said head and said handle, wherein said slider includes at least one set of markings thereon for indicating the amount of exposed bone between a posterior proximal portion of a tibia and a posterior edge of said head of said tibial sizer.

2. The tibial sizer as defined in claim 1, wherein said channel includes a pair of upper lips, in at least a portion of said head and at least a portion of said handle, for maintaining said slider within said channel.

3. The tibial sizer as defined in claim 1, wherein said channel extends through the entire length of said tibial sizer.

4. A tibial sizer for use during knee arthroplasty, said tibial sizer comprising:
 a head;
 a handle extending outwardly from said head;
 a channel extending along said tibial sizer in a longitudinal direction, through at least a portion of said head and at least a portion of said handle; and
 a slider configured and arranged to be slidably positioned within said channel, such that said slider is slidable within both said head and said handle,
 first set of markings for indication the amount of exposed bone between a posterior proximal portion of a tibia and a posterior edge of said head of said tibial sizer; and
 a second set of markings for indicating a suggested size of tibial base plate with respect to an anterior/posterior direction.

5. The tibial sizer as defined in claim 4, wherein said first set of markings are located on said slider, and provide said indication of exposed bone amount when viewed with respect to a terminal edge of said handle.

6. The tibial sizer as defined in claim 4, wherein said second set of markings are located on both said slider and said handle.

7. The tibial sizer as defined in claim 6, wherein said second set of markings comprise:
 indica on said handle representing different sizes of tibial base plates; and
 a pointer on said slider for pointing to the indicia on said handle to indicate a suggested size of tibial base plate with respect to the anterior/posterior direction.

8. The tibial sizer as defined in claim 7 wherein:
 said handle includes a first surface on one side thereof and a second surface on an opposite side thereof; and
 further wherein said second set of markings are visible when viewing both said first surface and said second surface.

9. The tibial sizer as defined in claim 4, further comprising a third set of markings, wherein said third set of markings comprise indicia on said slider representing different sizes of tibial base plates, wherein said third set of markings are not visible when said slider is inserted within said channel of said handle, but said third set of markings are visible when said slider is used without said handle, whereby said slider may be used for determining a suggested size of tibial base plate, with respect to the anterior/posterior direction, without said slider being inserted into said channel.

10. A system of tibial sizers for use during knee arthroplasty, said system comprising:
 a plurality of differently sized tibial sizers, wherein each tibial sizer includes:
  a head;
  a handle extending outwardly from said head; and
  a channel extending along said tibial sizer in a longitudinal direction, through at least a portion of said head and at least a portion of said handle; and
 a slider configured and arranged to be slidably positioned within each of said channels of said plurality of differently sized tibial sizers,
 a first set of markings for indicating the amount of exposed bone between a posterior proximal portion of a tibia and a posterior edge of said head of said tibial sizer;
 a second set of markings for indicating a suggested size of tibial base plate with respect to an anterior/posterior direction; and
 a third set of markings, wherein said third set of markings include indicia on said slider representing different sizes of tibial base plates, wherein said third set of markings are not visible when said slider is inserted within said channel of said handle, but said third set of markings are visible when said slider is used without said handle, whereby said slider may be used for determining a suggested size of tibial base plate, with respect to the anterior/posterior direction, without inserting said slider into one of said channels.

* * * * *